United States Patent [19]

Saito

[11] 4,355,644
[45] Oct. 26, 1982

[54] HEART RATE BIO-FEEDBACK SYSTEM

[76] Inventor: Iwao Saito, 33, Hon-cho, Eniwa, Hokkaido, Japan

[21] Appl. No.: 101,906

[22] Filed: Dec. 10, 1979

[30] Foreign Application Priority Data

Dec. 12, 1978 [JP] Japan .................. 53-152718

[51] Int. Cl.³ .............................................. A61B 5/04
[52] U.S. Cl. .................................. 128/689; 128/905
[58] Field of Search ............... 128/689, 706, 707, 709, 128/905, 732, 1 C

[56] References Cited

U.S. PATENT DOCUMENTS

| | | | |
|---|---|---|---|
| 3,384,075 | 5/1968 | Mitchell | 128/706 |
| 3,575,162 | 4/1971 | Gaarder | 128/905 |
| 3,576,185 | 4/1971 | Schulz et al. | 128/1 C |
| 3,858,574 | 1/1975 | Page | 128/689 |
| 3,942,516 | 3/1976 | Glynn et al. | 128/732 |
| 4,022,192 | 5/1977 | Laukien | 128/706 |
| 4,034,745 | 7/1977 | Bloom | 128/706 |

Primary Examiner—William E. Kamm
Attorney, Agent, or Firm—McGlew and Tuttle

[57] ABSTRACT

A heart rate bio-feedback system having a heart rate display means by which a patient recognizes his heart rate data that are obtained from the pulse or the heart beat signal detected from the patient, characterized in that the heart rate display means comprises a display means for displaying the momentary heart beat and a digital display circuit for displaying the integrated number of heart beats at a longer time interval.

4 Claims, 1 Drawing Figure

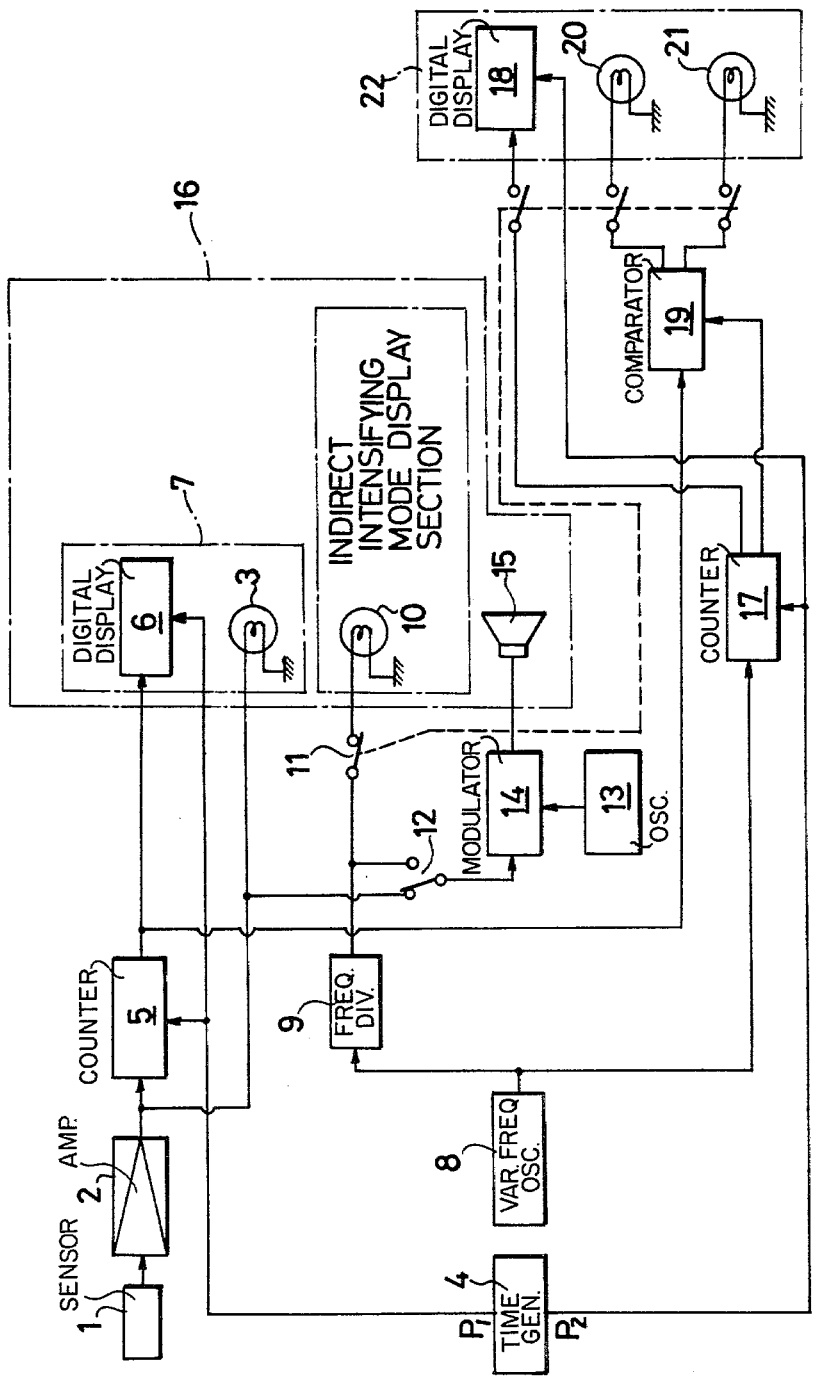

HEART RATE BIO-FEEDBACK SYSTEM

BACKGROUND OF THE INVENTION

The present invention relates to a heart rate bio-feedback system which performs heart rate bio-feedback control effectively by displaying the pulse or the heart beat signal detected from the patient's body so that the patient himself can recognize it as his heart rate data.

Apparatuses of this kind make it possible to easily self-control the autonomic nervous function of a patient by performing the bio-feedback of his physiological data through a medium such as light or sound as an intensifying factor in the bio-feedback, for use in recognizing the mind-body correlation objectively and training him in the heart rate control as a function of autonomic nerve, thereby the treatment and rehabilitation of patients having circulatory diseases involving tachy cardia, brady cardia, arrythmias and heart beat abnormalities being made possible. These systems can be applied to the treatment of diseases such as cardiac neurosis, neurocirculatory asthenia, sinus tachycardia, sinus bradycardia, and essential hypertension.

A system for directly controlling the increase and decrease of the heart rate by use of the so-called operant system is known, in which the heart rate, as compared with the standard heart beat, is displayed by a lamp or loudspeaker or the increase or decrease with respect to his own average heart beat period is displayed by changeover and, at the same time, the average heart beat period for 100 beats is digitally displayed. However, methods by the operant system which directs the adjustment of the heart rate in a certain direction are greatly affected by psychological factors, and thus, it is desirable to use these methods in conjunction with psychotherapy such as autonomic training.

SUMMARY OF THE INVENTION

It is an object of this invention to provide a heart rate bio-feedback system by which the heart rate bio-feedback can be performed easily by using intensifying factors more effective than those used in the foregoing operant system. This object is attained by a means for displaying the integrated number of heart beats at a certain time interval which is long enough to allow a patient to understand his condition, added to a means for displaying the momentary heart beat. Furthermore, the object of this invention can be attained more effectively by multiple use of the above-mentioned display means for the means of emitting an external stimulus such as intermittent light or sound at a proper time interval which serves to allow the patient to concentrate his mind on the situation at hand.

DESCRIPTION OF THE DRAWING

The accompanying FIGURE is a block diagram of the heart rate bio-feedback system according to the invention.

DETAILED DESCRIPTION OF THE PREFERRED EMBODIMENT

The present invention is explained by way of example as illustrated in the FIGURE. The heart rate bio-feedback system according to this invention consists of a bio-feedback display section which includes components with reference numbers from 1 through 6 and 12 through 15, an indirect intensifying mode display section which includes components with reference numbers from 8 through 15, and an operant mode display section which includes components with reference numbers 4, 8, 9, 11 and from 17 through 21, where some components are used in common. Finger tip pulse sensor 1, put on the finger tip of the patient, detects the pulse which is in synchronization with the heart beat. Amplifier 2 amplifies the pulse signal. Pulse indicator lamp 3 lights up each time a heart beat is detected and functions as a momentary heart beat indicating means. Standard time generator 4 produces signal P1 (1 pulse/min) and signal P2 (1 pulse/sec). Counter 5 counts the pulse signals from the amplifier 2 and are cleared by signal P1 after being sent out to digital display circuit 6. The digital display circuit 6 displays the count which is refreshed each time signal P1 is received. Variable frequency oscillator 8, by which the frequency can be preset in a range from 30 to 200 Hz, functions as an external stimulus source which is independent of the pulse signal. Frequency dividing circuit 9 divides the frequency of the signal from the variable frequency oscillator 8 by a factor of 60 to convert the pulse rate into the number of pulses per minute. Lamp 10 functions as a means for displaying the external stimulus signal which is the output of the frequency dividing circuit 9. Changeover switch 11 selects either of the display devices for the indirect intensifying mode and the operant mode (to be explained later). Oscillator 13 generates an audible frequency of 1 kHz, for example. Modulator 14 modulates the pulse signal or the external stimulus signal selected by the changeover switch 12 with a carrier generated by the oscillator 13. Loudspeaker 15 converts the output of the modulator 14, that is, the patient's heart beat or the external stimulus signal into sound.

The pulse indicator lamp 3 and the digital display circuit 6 constitute the bio-feedback display section 7, which digitally displays the number of heart beat. The stimulus indicator lamp 10 functions as an indirect intensifying mode display section which emits a stimulus signal independently of the pulse signal, whereas the bio-feedback display section 7 aims at intensifying the bio-feedback action by displaying the pulse signal data. The bio-feedback display section 7 and the indirect intensifying mode display section 10 constitute a multiplex intensifying mode display section 16. The loudspeaker 15 included in the multiplex intensifying mode display section 16 functions as a momentary heart beat signaling means or an external stimulus signaling means depending on the position of the changeover switch 12. In the foregoing circuit configuration, when the finger tip pulse sensor 1 is put on the finger of a patient afflicted with a circulatory disease involving heart beat or pulse abnormalities, or on a person who needs training on the autonomic nervous control, the pulse signal is amplified by the amplifier 2 and the momentary heart beat is indicated by the flashing of the pulse indicator lamp 3. The patient or trainee can know his heart rate data by looking at the pulse indicator lamp 3 and understanding the so-called mind-body correlation in psychosomatic medicine through the change in the heart beat interval caused by the feedback of the data, thereby, the heart rate control, that is, self-control being made possible. Thus effectiveness of the clinical application of such a display system has also been recognized.

According to the present invention, in addition to this display, the heart beat is integrated for one minute by the counter 5 and the number of heart beats per minute is displayed every minute by the digital display circuit 6. Therefore, long spanned bio-feedback becomes possible. The digital display of the number of heart beats per minute by the digital display circuit 6 will be easier for patients and a one-minute display interval allows patients time for recognizing and determining the relationship between the heart rate and emotion, that is, the mind-body correlation, so that self-control can be carried out effectively. Moreover, this also simplified the training on continuing the feedback. It was also found from experimental results that the bio-feedback display device equipped with the digital display circuit 6 in addition to the pulse indicator lamp 3 enables stable and powerful bio-feedback action which has not been possible by the prior art due to synergism of both factors.

Furthermore, the stimulus indicator lamp 10 included in the bio-feedback display section 7 emits an external stimulus by flashing a light in a frequency range from 30 to 180 cycles per minute, particularly between 60 and 70 cycles per minute, as predetermined in the variable frequency oscillator 8. This indirect intensifying mode is useful in easing the psychological strain of patients and also enhances the concentration of the mind which is necessary for the bio-feedback. This method makes it possible for patients to carry out effective bio-feedback, particularly those having conditions of neurosis and depression, for whom the foregoing bio-feedback is not successful. It was proved experimentally that external stimulus, particularly between 60 and 70 cycles per minute, gives a comfortable feeling to patients and is highly effective. A number of experimental results shows that the heart rate of patients of psychosomatic diseases involving neurosis and depression, for which the long-spanned feedback alone is not effective, can be controlled by the bio-feedback when an external stimulus of 60 cycles per minute, for example, is given.

The loudspeaker 15 emits a sound signal of the momentary heart beat or external stimulus as selected by the switch 12, in synchronization with the flashing light.

In this connection, the effectiveness of long spanned bio-feedback performed by the digital display circuit 6 can be expected not only when the integrated value is for one minute as mentioned above, but also when the integrated value is, for example, a value of 30 seconds displayed every 30 seconds or value of 15 seconds displayed every 15 seconds.

The multiplex intensifying mode display section as explained above is provided with an operant mode display section, which uses the standard time generator 4 and variable frequency oscillator 8 in common. This display section has the following circuit configuration. Counter 17 counts the frequency of the variable frequency oscillator 8 and is cleared by signal P2 every second, so that it functions equivalently as a counter which counts a cycle/minute signal every one minute. Comparator 19 compares the actual heart rate which is the output of the counter 5 with the standard heart rate which is the output of the counter 17. Digital display circuit 18, red lamp 20 and green lamp 21 constitute an operant mode display section 22. The digital display circuit 18 displays the standard heart rate which is refreshed at a certain time interval (60 s, 30 s, or 15 s). Either the red lamp 20 or the green lamp 21 lights up when the actual heart rate is higher or lower than the standard value.

When the bio-feedback system comprising circuits described above is used in the operant mode, the switch 11 is turned so that input signals are applied to the operant mode display section 22 and the standard heart rate is preset by adjusting the variable frequency oscillator 8. The doctor tells the patient to increase the heart rate or to blink on and off the red lamp 20 as frequently as possible for the case of bradycardia. In the case of tachycardia, the doctor tells the patient to decrease the heart rate or to blink on and off the green lamp 21 as frequently as possible.

It is obvious from the above explanation that the heart rate bio-feedback system according to the present invention, having an integrated heart beat display at a longer time interval for bio-feedback in addition to the momentary heart beat display, allows the patient to obtain an easier and more stable bio-feedback as compared with previous systems. Thus, the mind-body correlation can be understood objectively and easily from the heart rate change due to psychological stress and the heart rate self-control as an autonomic nervous function is also simplified. Moreover, this heart rate bio-feedback system provides a new method for stress-interview diagnosis, that is, the heart rate change under load of stress can be observed easily and objectively, resulting in better understanding of the mind-body correlation and more effective heart rate self-control.

The heart rate bio-feedback system according to the present invention can be applied effectively to the treatment of sinus tachycardia (and other mild cases of tachycardia), cardiac neurosis, neurocirculatory astheria, the so-called autonomic nervous ataxia, essential hypertension (generally, increased heart rate accompanied by increased blood pressure), sinus bradycardia, slight arrythmias (atrial and ventricle extrasystole), W.P.W. syndrome as well as other situations.

Furthermore, according to the present invention, by applying multiple external stimulus in addition to the long spanned bio-feedback, the heart rate bio-feedback is made possible for patients having neurosis and slight depression conditions whose self-control ability has deteriorated and effects of treatment of patients afflicted with the above-mentioned deseases can be expected.

What is claimed is:

1. A heart rate bio-feedback system comprising:
   detector means for detecting the pulse rate of a subject and converting it into a pulse rate signal;
   integrating circuit means for integrating said pulse rate signal over a set time interval;
   timing generator means for setting said time interval;
   display means comprising a display indicator means coupled to said detector means for displaying the momentary pulses of said pulse rate signal, and a digital display means coupled to said integrating circuit means for displaying the integrated pulse rate signal for said set time interval;
   variable controlled oscillator means for providing indicating signals independent of the pulse rate at a selective predetermined rate for use as an external stimulus for intensifying the biofeedback process, and
   an external stimulus visual display means for displaying said indicating signal simultaneously with the display of said momentary pulses.

2. A heart rate bio-feedback system as in claim 1 and further comprising an audio output, and switch means selectively coupling one of said indicating signals and said integrated pulse rate signals to said audio output.

3. A heart rate bio-feedback system as in claim 1 and further comprising an operant mode system comprising counter means for counting said selective predetermined rate for said certain time intervals, comparison means for comparing the output from said counter means with said pulse rate signal, and operant mode display means for displaying the results of said comparison means.

4. A heart rate bio-feedback system as in claim 3 and further comprising an external stimulus display means for displaying said indicating signals, and switch means for selecting one of said external stimulay display means and said operant mode display means.

* * * * *